Nov. 12, 1963 E. S. BOERNER Plant Pat. 2,302
ROSE PLANT
Filed Oct. 9, 1962
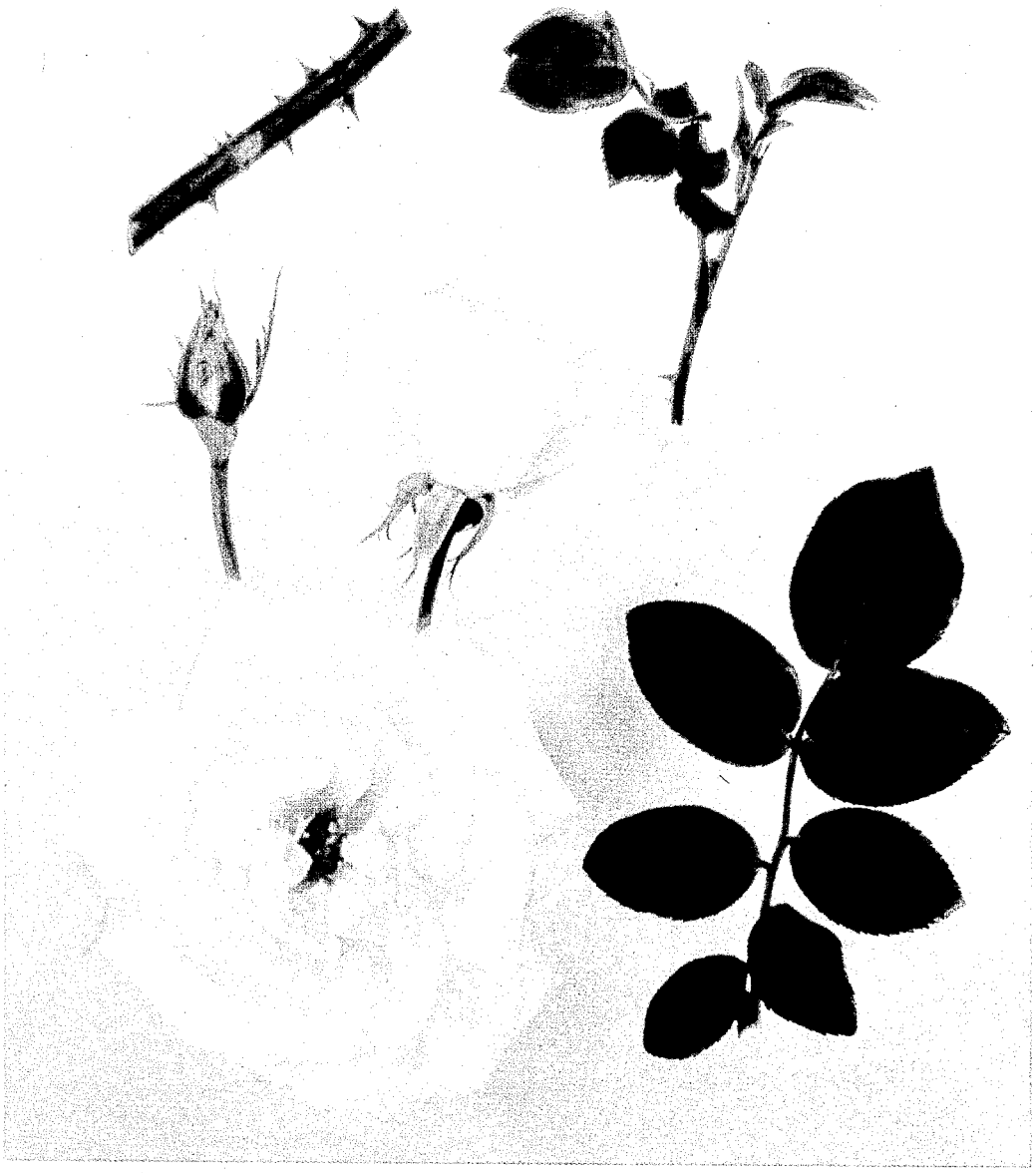
Inventor.
E. S. Boerner
By: Robb & Robb
Attorneys.

United States Patent Office

Plant Pat. 2,302

Patented Nov. 12, 1963

2,302

ROSE PLANT

Eugene S. Boerner, Newark, N.Y., assignor to Jackson & Perkins Company, Newark, N.Y., a corporation of New York Filed Oct. 9, 1962, Ser. No. 229,510
1 Claim. (Cl. Plt.—18)

The present invention relates to a new and distinct variety of rose plant of the hybrid tea class, which was originated by me by crossing the variety "Golden Masterpiece" (Plant Patent No. 1,284) with an unnamed and unpatented seedling of unidentified parentage.

The primary objective of this breeding was to produce a new large-flowered hybrid tea rose which bears flowers of pink color. This objective was fully achieved, along with other desirable improvements, as evidenced by the following unique combination of characteristics which are outstanding in the new variety and which distinguish it from its parents, as well as from all other varieties of which I am aware:

(1) Very clean foliage;
(2) Profuse and continuous habits of bloom;
(3) Attractive flower buds;
(4) Large open flowers; and
(5) A distinctive and attractive general color tonality of the flowers corresponding to Shrimp Pink, lightly overcast with Thulite Pink.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Golden Masterpiece."
*Pollen parent.*—An unamed seedling of unidentified parentage.

Classification:
*Botanic.*—Hybrid tea.
*Commercial.*—Hybrid tea.

*Flower*

(Observations made from specimens grown outdoors at Newark, New York, during the latter part of the month of June.)

Blooming habit: Recurrent—continuous; constantly produces profuse quantity of blooms.

Bud:
*Size.*—Medium.
*Form.*—Ovoid; is not affected by wet or hot weather.
*Color.*—When sepals first divide—Spinel Red, Plate 26. When petals begin to unfurl—Thulite Pink, Plate 26, lightly overcast with Spinel Pink, Plate 26. When half-blown: inside of petals—Seashell Pink, Plate 14, lightly overcast with La France Pink, Plate 1; reverse of petals—Thulite Pink, Plate 26, very lightly overcast with Spinel Pink, Plate 26.
*Sepals.*—Slightly branched; curl back when petals begin to unfurl. Color: inside—Courge Green, Plate 17; outside—Oil Green, Plate 5.
*Calyx.*—Color—Kildare Green, Plate 31. Shape— apple. Size—large. Aspect—smooth. Odor when rubbed—none.
*Peduncle.*—Length — medium. Aspect — smooth. Strength—erect; heavy. Color—Deep Chrysolite Green, Plate 31.
*Opening.*—Opens up well; is not affected by adverse weather conditions.

Bloom:
*Size.*—Large. Average size when fully expanded—from 5 inches to 5½ inches.
*Borne.*—Both singly and several together.
*Stems.*—Medium length; strong.
*Form (when first open).*—Cupped. Permanence—retains its form to the end, but outer petals curl back.
*Petalage.*—Double (full but open center). Number of petals under normal conditions—from 35 to 40.
*Color.*—Center of flower—Pale Salmon Color, Plate 14, lightly overcast with Eosine Pink, Plate 1. Outer petals—La France Pink, Plate 1, very lightly overcast with Thulite Pink, Plate 26. Base of petals (aiglet)—Lemon Chrome, Plate 4. Inside of petals—Shrimp Pink, Plate 1, lightly overcast with Thulite Pink, Plate 26. Reverse of petals—Hermosa Pink, Plate 1, very lightly overcast with Thulite Pink, Plate 26. General tonality from a distance—Shrimp Pink, Plate 1, lightly overcast with Thulite Pink, Plate 26.
*Discoloration.*—General tonality at end of first day—Pale Salmon color, Plate 14, lightly overcast with Eosine Pink, Plate 1. Second day—Shrimp Pink, Plate 1, lightly overcast with Thulite Pink, Plate 26. Third day—Shrimp Pink, Plate 1, lightly overcast with Thulite Pink, Plate 26.

Petals:
*Texture.*—Leathery; is not affected by wet or hot weather.
*Appearance.*—Inside—satiny. Outside—shiny.
*Form.*—Oval; slightly notched.
*Arrangement.* — Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital Organs*

Stamens, anthers: Medium size; many; regularly arranged around styles. Color—Orange Buff, Plate 3.
Stamens, filaments (threads): Medium length. Color—Baryta Yellow, Plate 4.
Pollen: Color—Capucine Buff, Plate 3.
Styles: Bunched; uneven length; medium length; thin.
Stigmas: Color—Naples Yellow, Plate 4.
Ovaries: All enclosed in calyx.
Hips: None.
Seeds: None.

*Plant*

Form: Bush.
Growth: Vigorous; upright.
Foliage: Compound of 3–7 leaflets.
*Size.*—Large.
*Quantity.*—Normal; very clean.
*Color.*—New foliage: upper side—Oil Green, Plate 5, lightly overcast with Victoria Lake, Plate 1; under side—Van Dyke Red, Plate 13. Old foliage: upper side—Dark Dull Yellow-Green, Plate 32; under side—Bice Green, Plate 17.
*Shape.*—Oval pointed.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Light Bice Green, Plate 17. Under side—smooth.

*Stipules.*—Medium length; smooth.

Wood:

*New wood.*—Color—Hessian Brown, Plate 13. Bark—smooth.

*Old wood.*—Color—Dark Cress Green, Plate 31. Bark—Smooth.

Thorns:

*Thorns.*—Quantity: on main stalks from base—ordinary; on laterals from stalk—ordinary. Form—narrow base; medium length; hooked downward.

Color (when young)—Pompeian Red, Plate 13. Position—irregular.

*Prickles.*—Quantity: on main stalks—none; on laterals—none.

*Short needles.*—Quanity: on main stalks—none; on laterals—none.

I claim:

A new and distinct variety of rose plant of the hybrid tea class, substantially as herein shown and described, characterized particularly as to novelty by the unique combination of very clean foliage, profuse and continuous habits of bloom, attractive flower buds, large open flowers, and a distinctive and attractive general color tonality of the flowers corresponding to Shrimp Pink, lightly overcast with Thulite Pink.

No references cited.